US012606624B2

(12) United States Patent
Zhuang et al.

(10) Patent No.: US 12,606,624 B2
(45) Date of Patent: Apr. 21, 2026

(54) ANTIBODY THAT SPECIFICALLY BINDS TO HUMAN CTLA4 AND MEDICAMENTS AND KITS COMPRISING THE SAME

(71) Applicant: NovoMab BioPharmaceuticals Inc, Nanjing (CN)

(72) Inventors: Weiliang Zhuang, Nanjing (CN); Lili Pei, Nanjing (CN)

(73) Assignee: NovoMab BioPharmaceuticals Inc, Nanjing (CN)

( * ) Notice: Subject to any disclaimer, the term of this patent is extended or adjusted under 35 U.S.C. 154(b) by 494 days.

(21) Appl. No.: 18/456,503

(22) Filed: Aug. 27, 2023

(65) Prior Publication Data

US 2024/0018243 A1      Jan. 18, 2024

Related U.S. Application Data

(63) Continuation of application No. PCT/CN2022/127521, filed on Oct. 26, 2022.

(30) Foreign Application Priority Data

Oct. 21, 2021    (CN) .......................... 202111229808.3

(51) Int. Cl.
*A61P 35/00*          (2006.01)
*C07K 16/28*         (2006.01)
(52) U.S. Cl.
CPC .......... *C07K 16/2818* (2013.01); *A61P 35/00* (2018.01); *C07K 2317/52* (2013.01); *C07K 2317/565* (2013.01); *C07K 2317/622* (2013.01)

(58) Field of Classification Search
CPC ............ C07K 16/2818; C07K 2317/52; C07K 2317/565; C07K 2317/622; C07K 2317/22; C07K 2317/24; C07K 2317/569; C07K 2317/76; C07K 2317/92; C07K 2317/732; C07K 2317/94; A61P 35/00; A61P 31/00; A61P 33/00; A61K 2039/505
USPC ....................................... 424/133.1
See application file for complete search history.

(56) References Cited

FOREIGN PATENT DOCUMENTS

| CN | 109195665 A | 1/2019 |
| CN | 110760002 A | 2/2020 |
| CN | 113754770 A | 12/2021 |

*Primary Examiner* — Yan Xiao
(74) *Attorney, Agent, or Firm* — Nitin Kaushik

(57)          ABSTRACT

The present invention discloses an antibody that specifically binds to human CTLA4, comprising three complementarily-determining regions; the three complementarity-determining regions are respectively: CDR1 with an amino acid sequence as shown in SEQ ID NO: 1, CDR2 with an amino acid sequence as shown in SEQ ID NO: 2, and CDR3 with an amino acid sequence as shown in SEQ ID NO: 3. Also disclosed are medicaments and kits comprising the antibodies described above. The antibodies of the present invention exhibit, but are not limited to, the following properties: (1) high affinity and specificity with human CTLA4; (2) able to block the interaction of CTLA4 with CD86 or CD80; (3) able to specifically bind to CTLA4 overexpressing cells; (4) enhancing activation of PBMC and/or T cells; (5) inhibiting tumor growth.

12 Claims, 7 Drawing Sheets

Specification includes a Sequence Listing.

| | HCA13 | HCA14 | HCA15 | CT-A1 | CTC |
|---|---|---|---|---|---|
| EC50 | 82.69 | 8.087 | 165.1 | 6.775 | 7.385 |

A

| | CT-A1 | HCA11 | HCA12 | HCA13 |
|---|---|---|---|---|
| EC50 | 4.351 | 657.4 | 1141 | 71.62 |

B

HCA14-F1 direct binding activity

| EC50 | 0.6364 |
|---|---|

C

SEQUENCE LISTING

```
Sequence total quantity: 26
SEQ ID NO: 1              moltype = AA   length = 5
FEATURE                   Location/Qualifiers
source                    1..5
                          mol_type = protein
                          organism = synthetic construct
SEQUENCE: 1
INHMA                                                              5

SEQ ID NO: 2              moltype = AA   length = 16
FEATURE                   Location/Qualifiers
source                    1..16
                          mol_type = protein
                          organism = synthetic construct
SEQUENCE: 2
GVNSRGTTNY VDSVKG                                                  16

SEQ ID NO: 3              moltype = AA   length = 7
FEATURE                   Location/Qualifiers
source                    1..7
                          mol_type = protein
                          organism = synthetic construct
SEQUENCE: 3
LGGAVAA                                                            7

SEQ ID NO: 4              moltype = AA   length = 115
FEATURE                   Location/Qualifiers
source                    1..115
                          mol_type = protein
                          organism = synthetic construct
SEQUENCE: 4
QVQLQESGGG LVQAGGSLRL SCAASGSIFS INHMAWYRQA PGKQRELVAG VNSRGTTNYV  60
DSVKGRFTIS RDNAKNMVYL LMNSLKPEDT AVYYCRALGG AVAAWGQGTQ VTVSS       115

SEQ ID NO: 5              moltype = AA   length = 98
FEATURE                   Location/Qualifiers
source                    1..98
                          mol_type = protein
                          organism = synthetic construct
SEQUENCE: 5
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAK                          98

SEQ ID NO: 6              moltype = AA   length = 115
FEATURE                   Location/Qualifiers
source                    1..115
                          mol_type = protein
                          organism = synthetic construct
SEQUENCE: 6
EVQLLESGGG LVQPGGSLRL SCAASGFTFS INHMAWYRQA PGKGLELVAG VNSRGTTNYV  60
DSVKGRFTIS RDNSKNTLYL QMNSLRAEDT AVYYCAALGG AVAAWGQGTL VTVSS       115

SEQ ID NO: 7              moltype = AA   length = 115
FEATURE                   Location/Qualifiers
source                    1..115
                          mol_type = protein
                          organism = synthetic construct
SEQUENCE: 7
EVQLLESGGG LVQPGGSLRL SCAASGSIFS INHMAWYRQA PGKGLELVAG VNSRGTTNYV  60
DSVKGRFTIS RDNSKNTLYL QMNSLRAEDT AVYYCAALGG AVAAWGQGTL VTVSS       115

SEQ ID NO: 8              moltype = AA   length = 115
FEATURE                   Location/Qualifiers
source                    1..115
                          mol_type = protein
                          organism = synthetic construct
SEQUENCE: 8
EVQLLESGGG LVQPGGSLRL SCAASGSIFS INHMAWYRQA PGKGLELVAG VNSRGTTNYV  60
DSVKGRFTIS RDNSKNTLYL QMNSLRAEDT AVYYCRALGG AVAAWGQGTL VTVSS       115

SEQ ID NO: 9              moltype = AA   length = 115
FEATURE                   Location/Qualifiers
source                    1..115
                          mol_type = protein
                          organism = synthetic construct
SEQUENCE: 9
EVQLLESGGG LVQPGGSLRL SCAASGSIFS INHMAWYRQA PGKQRELVAG VNSRGTTNYV  60
DSVKGRFTIS RDNSKNTLYL QMNSLRAEDT AVYYCRALGG AVAAWGQGTL VTVSS       115
```

```
SEQ ID NO: 10              moltype = AA   length = 115
FEATURE                    Location/Qualifiers
source                     1..115
                           mol_type = protein
                           organism = synthetic construct
SEQUENCE: 10
EVQLLESGGG LVQPGGSLRL SCAASGSIFS INHMAWYRQA PGKGLELVAG VNSRGTTNYV   60
DSVKGRFTIS RDNSKNMVYL QMNSLRAEDT AVYYCRALGG AVAAWGQGTL VTVSS        115

SEQ ID NO: 11              moltype = AA   length = 359
FEATURE                    Location/Qualifiers
source                     1..359
                           mol_type = protein
                           organism = synthetic construct
SEQUENCE: 11
QVQLQESGGG LVQAGGSLRL SCAASGSIFS INHMAWYRQA PGKQRELVAG VNSRGTTNYV   60
DSVKGRFTIS RDNAKNMVYL LMNSLKPEDT AVYYCRALGG AVAAWGQGTQ VTVSSGGGGS  120
GGGGSGGGGS ESKYGPPCPP CPAPEFLGGP SVFLFPPKPK DTLMISRTPE VTCVVVDVSQ  180
EDPEVQFNWY VDGVEVHNAK TKPREEQFNS TYRVVSVLTV LHQDWLNGKE YKCKVSNKGL  240
PSSIEKTISK AKGQPREPQV YTLPPSQEEM TKNQVSLTCL VKGFYPSDIA VEWESNGQPE  300
NNYKTTPPVL DSDGSFFLYS RLTVDKSRWQ EGNVFSCSVM HEALHNHYTQ KSLSLSLGK   359

SEQ ID NO: 12              moltype = AA   length = 359
FEATURE                    Location/Qualifiers
source                     1..359
                           mol_type = protein
                           organism = synthetic construct
SEQUENCE: 12
EVQLLESGGG LVQPGGSLRL SCAASGFTFS INHMAWYRQA PGKGLELVAG VNSRGTTNYV   60
DSVKGRFTIS RDNSKNTLYL QMNSLRAEDT AVYYCAALGG AVAAWGQGTL VTVSSGGGGS  120
GGGGSGGGGS ESKYGPPCPP CPAPEFLGGP SVFLFPPKPK DTLMISRTPE VTCVVVDVSQ  180
EDPEVQFNWY VDGVEVHNAK TKPREEQFNS TYRVVSVLTV LHQDWLNGKE YKCKVSNKGL  240
PSSIEKTISK AKGQPREPQV YTLPPSQEEM TKNQVSLTCL VKGFYPSDIA VEWESNGQPE  300
NNYKTTPPVL DSDGSFFLYS RLTVDKSRWQ EGNVFSCSVM HEALHNHYTQ KSLSLSLGK   359

SEQ ID NO: 13              moltype = AA   length = 359
FEATURE                    Location/Qualifiers
source                     1..359
                           mol_type = protein
                           organism = synthetic construct
SEQUENCE: 13
EVQLLESGGG LVQPGGSLRL SCAASGSIFS INHMAWYRQA PGKGLELVAG VNSRGTTNYV   60
DSVKGRFTIS RDNSKNTLYL QMNSLRAEDT AVYYCAALGG AVAAWGQGTL VTVSSGGGGS  120
GGGGSGGGGS ESKYGPPCPP CPAPEFLGGP SVFLFPPKPK DTLMISRTPE VTCVVVDVSQ  180
EDPEVQFNWY VDGVEVHNAK TKPREEQFNS TYRVVSVLTV LHQDWLNGKE YKCKVSNKGL  240
PSSIEKTISK AKGQPREPQV YTLPPSQEEM TKNQVSLTCL VKGFYPSDIA VEWESNGQPE  300
NNYKTTPPVL DSDGSFFLYS RLTVDKSRWQ EGNVFSCSVM HEALHNHYTQ KSLSLSLGK   359

SEQ ID NO: 14              moltype = AA   length = 359
FEATURE                    Location/Qualifiers
source                     1..359
                           mol_type = protein
                           organism = synthetic construct
SEQUENCE: 14
EVQLLESGGG LVQPGGSLRL SCAASGSIFS INHMAWYRQA PGKGLELVAG VNSRGTTNYV   60
DSVKGRFTIS RDNSKNTLYL QMNSLRAEDT AVYYCRALGG AVAAWGQGTL VTVSSGGGGS  120
GGGGSGGGGS ESKYGPPCPP CPAPEFLGGP SVFLFPPKPK DTLMISRTPE VTCVVVDVSQ  180
EDPEVQFNWY VDGVEVHNAK TKPREEQFNS TYRVVSVLTV LHQDWLNGKE YKCKVSNKGL  240
PSSIEKTISK AKGQPREPQV YTLPPSQEEM TKNQVSLTCL VKGFYPSDIA VEWESNGQPE  300
NNYKTTPPVL DSDGSFFLYS RLTVDKSRWQ EGNVFSCSVM HEALHNHYTQ KSLSLSLGK   359

SEQ ID NO: 15              moltype = AA   length = 359
FEATURE                    Location/Qualifiers
source                     1..359
                           mol_type = protein
                           organism = synthetic construct
SEQUENCE: 15
EVQLLESGGG LVQPGGSLRL SCAASGSIFS INHMAWYRQA PGKQRELVAG VNSRGTTNYV   60
DSVKGRFTIS RDNSKNTLYL QMNSLRAEDT AVYYCRALGG AVAAWGQGTL VTVSSGGGGS  120
GGGGSGGGGS ESKYGPPCPP CPAPEFLGGP SVFLFPPKPK DTLMISRTPE VTCVVVDVSQ  180
EDPEVQFNWY VDGVEVHNAK TKPREEQFNS TYRVVSVLTV LHQDWLNGKE YKCKVSNKGL  240
PSSIEKTISK AKGQPREPQV YTLPPSQEEM TKNQVSLTCL VKGFYPSDIA VEWESNGQPE  300
NNYKTTPPVL DSDGSFFLYS RLTVDKSRWQ EGNVFSCSVM HEALHNHYTQ KSLSLSLGK   359

SEQ ID NO: 16              moltype = AA   length = 359
FEATURE                    Location/Qualifiers
source                     1..359
                           mol_type = protein
```

-continued

```
                    organism = synthetic construct
SEQUENCE: 16
EVQLLESGGG LVQPGGSLRL SCAASGSIFS INHMAWYRQA PGKGLELVAG VNSRGTTNYV    60
DSVKGRFTIS RDNSKNMVYL QMNSLRAEDT AVYYCRALGG AVAAWGQGTL VTVSSGGGGS   120
GGGGSGGGGS ESKYGPPCPP CPAPEFLGGP SVFLFPPKPK DTLMISRTPE VTCVVVDVSQ   180
EDPEVQFNWY VDGVEVHNAK TKPREEQFNS TYRVVSVLTV LHQDWLNGKE YKCKVSNKGL   240
PSSIEKTISK AKGQPREPQV YTLPPSQEEM TKNQVSLTCL VKGFYPSDIA VEWESNGQPE   300
NNYKTTPPVL DSDGSFFLYS RLTVDKSRWQ EGNVFSCSVM HEALHNHYTQ KSLSLSLGK    359

SEQ ID NO: 17             moltype = AA  length = 362
FEATURE                   Location/Qualifiers
source                    1..362
                          mol_type = protein
                          organism = synthetic construct
SEQUENCE: 17
EVQLLESGGG LVQPGGSLRL SCAASGSIFS INHMAWYRQA PGKQRELVAG VNSRGTTNYV    60
DSVKGRFTIS RDNSKNTLYL QMNSLRAEDT AVYYCRALGG AVAAWGQGTL VTVSSGGGGS   120
GGGGSGGGGS EPKSCDKTHT CPPCPAPELL GGPSVFLFPP KPKDTLMISR TPEVTCVVVD   180
VSHEDPEVKF NWYVDGVEVH NAKTKPREEQ YNSTYRVVSV LTVLHQDWLN GKEYKCKVSN   240
KALPAPIEKT ISKAKGQPRE PQVYTLPPSR EEMTKNQVSL TCLVKGFYPS DIAVEWESNG   300
QPENNYKTTP PVLDSDGSFF LYSKLTVDKS RWQQGNVFSC SVMHEALHNH YTQKSLSLSP   360
GK                                                                 362

SEQ ID NO: 18             moltype = AA  length = 229
FEATURE                   Location/Qualifiers
source                    1..229
                          mol_type = protein
                          organism = synthetic construct
SEQUENCE: 18
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPCQEEM TKNQVSLWCL VKGFYPSDIA VEWESNGQPE NNYKTTPPVL   180
DSDGSFFLYS RLTVDKSRWQ EGNVFSCSVM HEALHNHYTQ KSLSLSLGK              229

SEQ ID NO: 19             moltype = AA  length = 359
FEATURE                   Location/Qualifiers
source                    1..359
                          mol_type = protein
                          organism = synthetic construct
SEQUENCE: 19
EVQLLESGGG LVQPGGSLRL SCAASGSIFS INHMAWYRQA PGKQRELVAG VNSRGTTNYV    60
DSVKGRFTIS RDNSKNTLYL QMNSLRAEDT AVYYCRALGG AVAAWGQGTL VTVSSGGGGS   120
GGGGSGGGGS ESKYGPPCPP CPAPEFLGGP SVFLFPPKPK DTLMISRTPE VTCVVVDVSQ   180
EDPEVQFNWY VDGVEVHNAK TKPREEQFNS TYRVVSVLTV LHQDWLNGKE YKCKVSNKGL   240
PSSIEKTISK AKGQPREPQV CTLPPSQEEM TKNQVSLSCA VKGFYPSDIA VEWESNGQPE   300
NNYKTTPPVL DSDGSFFLVS RLTVDKSRWQ EGNVFSCSVM HEALHNHYTQ KSLSLSLGK    359

SEQ ID NO: 20             moltype = AA  length = 118
FEATURE                   Location/Qualifiers
source                    1..118
                          mol_type = protein
                          organism = synthetic construct
SEQUENCE: 20
QVQLVESGGG VVQPGRSLRL SCAASGFTFS SYTMHWVRQA PGKGLEWVTF ISYDGNNKYY    60
ADSVKGRFTI SRDNSKNTLY LQMNSLRAED TAIYYCARTG WLGPFDYWGQ GTLVTVSS     118

SEQ ID NO: 21             moltype = AA  length = 108
FEATURE                   Location/Qualifiers
source                    1..108
                          mol_type = protein
                          organism = synthetic construct
SEQUENCE: 21
EIVLTQSPGT LSLSPGERAT LSCRASQSVG SSYLAWYQQK PGQAPRLLIY GAFSRATGIP    60
DRFSGSGSGT DFTLTISRLE PEDFAVYYCQ QYGSSPWTFG QGTKVEIK                108

SEQ ID NO: 22             moltype = AA  length = 397
FEATURE                   Location/Qualifiers
source                    1..397
                          mol_type = protein
                          organism = synthetic construct
SEQUENCE: 22
MACLGFQRHK AQLNLAARTW PCTLLFFLLF IPVFCKAMHV AQPAVVLASS RGIASFVCEY    60
ASPGKATEVR VTVLRQADSQ VTEVCAATYM MGNELTFLDD SICTGTSSGN QVNLTIQGLR   120
AMDTGLYICK VELMYPPPYY LGIGNGTQIY VIDPEPCPDS DGSGSEPKSC DKTHTCPPCP   180
APELLGGPSV FLFPPKPKDT LMISRTPEVT CVVVDVSHED PEVKFNWYVD GVEVHNAKTK   240
PREEQYNSTY RVVSVLTVLH QDWLNGKEYK CKVSNKALPA PIEKTISKAK GQPREPQVYT   300
LPPSRDELTK NQVSLTCLVK GFYPSDIAVE WESNGQPENN YKTTPPVLDS DGSFFLYSKL   360
TVDKSRWQQG NVFSCSVMHE ALHNHYTQKS LSLSPGK                           397
```

-continued

```
SEQ ID NO: 23              moltype = DNA   length = 23
FEATURE                    Location/Qualifiers
source                     1..23
                           mol_type = other DNA
                           organism = synthetic construct
SEQUENCE: 23
gtcctggctg ctcttctaca agg                                     23

SEQ ID NO: 24              moltype = DNA   length = 23
FEATURE                    Location/Qualifiers
source                     1..23
                           mol_type = other DNA
                           organism = synthetic construct
SEQUENCE: 24
ggtacgtgct gttgaactgt tcc                                     23

SEQ ID NO: 25              moltype = DNA   length = 47
FEATURE                    Location/Qualifiers
source                     1..47
                           mol_type = other DNA
                           organism = synthetic construct
SEQUENCE: 25
accgtggccc aggcggccca ggtgcagctg caggagtctg grggagg           47

SEQ ID NO: 26              moltype = DNA   length = 39
FEATURE                    Location/Qualifiers
source                     1..39
                           mol_type = other DNA
                           organism = synthetic construct
SEQUENCE: 26
gtgctggccg gcctggccgc tggagacggt gacctgggt                    39
```

ANTIBODY THAT SPECIFICALLY BINDS TO HUMAN CTLA4 AND MEDICAMENTS AND KITS COMPRISING THE SAME

CROSS-REFERENCE TO RELATED APPLICATIONS

The application claims priority to Chinese patent application No, 2021112298083, filed on Oct. 21, 2021, the entire contents of which are incorporated herein by reference.

SEQUENCE LISTING

The sequence listing xml file submitted herewith, named "WIUS239251P_SeqList.xml", created on Aug. 24, 2023, and having a file size of 27750.4 bytes, is incorporated by reference herein.

TECHNICAL FIELD

The present invention is in the field of biomedicine and in particular relates to an antibody that specifically binds to human CTLA4 and medicaments and kits comprising the same.

BACKGROUND

Cytotoxic T lymphocyte-associated antigen 4 (CTLA4), also known as CD152, the fourth specific antigen gene found in cytotoxic T lymphocytes. The gene is located on human chromosome 2 at position 2q33, which is 6,174 bp in length and contains 3 exons and 2 introns. The major function of the extracellular segment of the CTLA4 protein is to bind to its cognate ligand B7 molecule. More than three B7 molecules have now been discovered, named B7-1 (CD80), B7-2 (CD86), B7-3, etc. Its intracellular end has only 36 amino acids, and this part of the amino acid sequence constitutes a structure called ITIM (immune tyrosine inhibitory motif), which converts a foreign signal bound to the B7 molecule into a negative regulatory signal of the cell.

CTLA4 is mainly expressed in T cells, is t transmembrane receptor on T cells, shares the ligand of B7 molecule with CD28, and the binding force of the extracellular region of CTLA4 to B7 molecule is 20 to 100 times greater than that of CD28, thus making it superior to the ligand of CD28. After binding to the B7 molecule, CTLA4 induces T cell anergy and is involved in the negative regulation of the immune response, while CD28 transmits stimulatory signals. CTLA4 is also found in regulatory T cells (Treg) and contributes to their inhibitory function.

During tumorigenesis, CTLA4 binds to its ligand B7 to generate an inhibitory signal, which inhibits T cell activation and protects tumor cells from T lymphocyte attack. Thus, by blocking the binding of CTLA4 to B7 molecules, the proliferation of immune cells can be stimulated to induce or enhance an anti-tumor immune response. Studies have shown that molecules targeting CTLA4 produce antitumor, effects by two mechanisms: (1) reducing the immunosuppressive signal of tumor-specific effector T cells, such as CD8+ T cells, leads to clonal expansion thereof and enhances tumor suppressor activity. (2) removing tumor-induced regulatory T cells (Treg), Treg cells can suppress the immune response to tumor-associated antigens. Currently, Ipilimumab and Tremelimumab targeting CTLA4 have been used clinically and widely for the treatment of melanoma, renal cancer, prostate cancer, lung cancer, etc. but both antibodies are traditional IgG antibodies containing heavy and light chains, and the clinical efficacy is not outstanding. Therefore, the development of novel CTLA4 antibodies, especially single domain antibodies, is of great significance for the development of immunotherapy drugs for the treatment of tumors.

SUMMARY

The present invention addresses the above-mentioned deficiencies of the prior art by providing an antibody that specifically binds to human CTLA4 and medicaments and kits comprising the same. The present invention is an antibody that specifically binds to CTLA4, providing a molecule that binds to CTLA4 that exhibits, but is not limited, to, the following properties: (1) high affinity and specificity with human CTLA4; (2) able to block the interaction of CTLA4 with CD86 or CD80; (3) able to specifically bind to CTLA4 overexpressing cells; (4) enhancing activation of PBMC and/or T cells; (5) inhibiting tumor growth.

The specific technical solutions are as follows:

It is an object of the present invention to provide an antibody that specifically binds to human CTLA4, comprising three complementarity-determining regions;

the three complementarity-determining regions are respectively: CDR1 with an amino acid sequence as shown in SEQ ID NO: 1, CDR2 with an amino acid sequence as shown in SEQ ID NO: 2, and CDR3 with an amino acid sequence as shown in SEQ ID NO: 3.

The beneficial effects of the above technical solution are: the CDR region provided by the present invention allows antibodies that bind CTLA4 to have high affinity and specificity for human CTLA4.

Further, the antibody is a single domain antibody, preferably a heavy chain single domain antibody.

Still further, the single domain antibody comprises any one of the following amino acid sequences: SEQ ID NO: 4, SEQ ID NO: 8, SEQ ID NO: 9, or SEQ ID NO: 10.

Still more preferably, the amino acid sequence of the single domain antibody has at least 90% overall sequence identity with amino acid sequences SEQ ID NO: 4 and SEQ ID NO: 9.

The beneficial effects of the above technical solution are: the present invention provides antibodies that bind CTLA4 with high affinity and specificity for binding to human CTLA4, with enhanced activation of PBMC and/or T cells and inhibition of tumor growth.

Further, the antibody further comprises an, immunoglobulin FC region.

Still further, the immunoglobulin FC region is that of a human immunoglobulin FC region, preferably human or IgG1 or IgG4.

Still more preferably, the antibody comprises any one of the following amino acid sequences: SEQ ID NO: 11, SEQ ID NO: 14, SEQ ID NO: 15, SEQ ID NO: 16, SEQ ID NO: 17.

The beneficial effects of the above technical solution are: the present invention provides antibodies that bind CTLA4 with high affinity and specificity for human CTLA4, with enhanced activation of PBMC and/or T cells and inhibition of tumor growth. The single domain antibodies mediate ADCC activity by binding to antigenic sites of target cells (e.g. Treg cells) and PC receptor sites of effector cells, thereby killing the target cells. On the other hand, the single domain antibody has a longer half-life and better stability in vivo.

Further, the antibody has at least one of the following characteristics:

A. binding to human CTLA4;

B. blocking the interaction of CTLA4 with CD86 or CD80;

C. enhancing activation of PBMC and/or T cells;

D. inhibition of tumor growth.

It is a second object of the present invention to provide a pharmaceutical composition, comprising a medicament comprising the antibody that specifically binds to human CTLA4 as described above for the treatment or alleviation of cancer and/or infectious diseases.

It is a third object of the pit cut invention to provide the use of the antibody that specifically binds to human CTLA4 as described above in the preparation of a medicament.

It is a fourth object of the present invention to provide a kit comprising the antibody that specifically binds to human CTLA4 as described above for diagnosing a disease associated with CTLA4; the CTLA4-associated disease is a tumor and/or infectious disease associated with high expression of CTLA4.

The beneficial effects of using the above technical solution are: the antibody that binds to CTLA4 of the present invention can be used in a kit to effectively detect and diagnose related diseases.

DETAILED DESCRIPTION OF THE EMBODIMENTS

Figure 1:
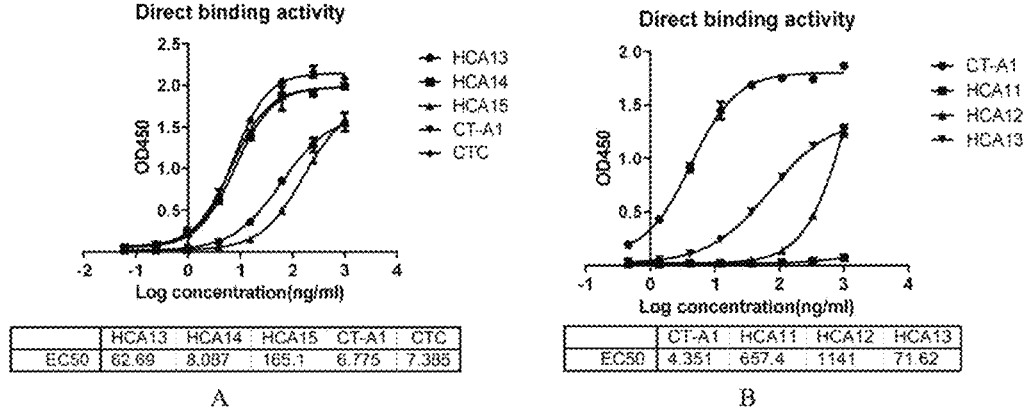
FIG. 1 shows the results of the binding activity of the antibody of Example 4 to CTLA4 recombinant protein; the results showed that different antibodies had different activities with CTLA4 recombinant protein, wherein the EC50 of CA1-F4 was 6.775 ng/mL, the EC50 of HCA14-F4 was 8.087 ng/mL and the EC50 of HCA14-F1 was 0.6364 ng/mL.
Figure 1:
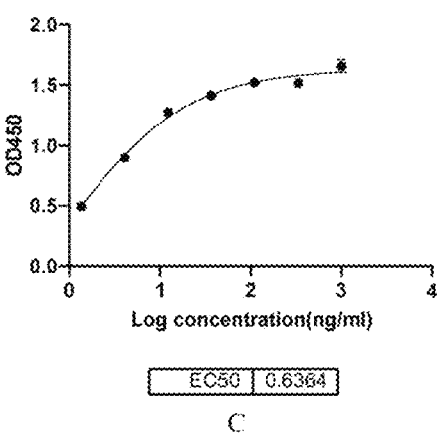

The principles and features of the present invention are described below with reference to examples, which are intended to be illustrative only and are not intended to limit the scope of the invention.

Example 1: Screening of CTLA4 Antibody

1. Immunization of Alpaca

An expression plasmid PCDNA3.1-CTLA4-FC of CTLA4-FC fusion, protein (the amino acid sequence is as shown in SEQ ID NO: 22) was constructed, and the plasmid was transiently transfected into 293F cells and cultured for 5 days. The supernatant was collected and purified by proteinA (GE) affinity chromatography to obtain CTLA4-FC fusion protein.

TiterMax Gold adjuvant and CTLA4-FC fusion protein were mixed and emulsified for immunization. Two sites were injected into the bilateral hip muscles of the alpaca, 0.2 mL at each site, once a week, 500 µg for the first time and 200 µg for each subsequent time. The immunization lasted for 5 weeks, in the 4th week, blood was taken for antibody titer assay, and in the 5th week, 20 mL of peripheral blood was taken.

2. VHH Antibody Library Construction

Lymphocytes from peripheral blood were separated using lymphocyte separation solution, RNA was extracted by purelink RNA Micro kit (Thermo), and cDNA was prepared by reverse transcription using PrimeScript II 1st Strand cDNA Synthesis Kit (Thermo). Using cDNA as a template, an antibody fragment is amplified using an upstream primer (nucleotide sequence as shown in SEQ ID NO: 23, specifically 5'-GTCCTGGCTGCICTTCTACAAGG-3') and a downstream primer (nucleotide sequence as shown in SEQ ID NO: 24, specifically 5'-GTCCTGGCTGCTCTTCTA-CAAGG-3') as primers, wherein the VHH fragment has a size of about 700 bp and the normal VH fragment has a size of about 1000 bp.

The gel recovery kit recovered a VHH fragment of about 700 bp. VHH variable region fragments were amplified using VHH fragments as templates and VHH-F (SfiI) (nucleotide sequence as shown in SEQ ID NO: 25, specifically 5'-ACCGTGGCCCAGGCGGCCCAGGTGCAGCTGCAG-GAGTCTGGRGGAGG-3') and VHH-R (SfiI) (nucleotide sequence as shown in SEQ ID NO: 26, specifically 5'-GTGCTGGCCGGCCTGGCCGCTGGA-GACGGTGACCTGGGT-3') as primers.

Antibody libraries were constructed by enzymatically ligating VHH variable regions into Pcomb3 phage plasmids through StiI restriction sites.

3. Screening of CTLA4 Antibodies

CTLA4 antibody screening was then performed, by phage display, specific steps are as follows:

A. Electroporation: 5 µL of antibody library was transferred into 50 µL of E. coli TG1 competent cells, mixed well, added to the electroporation cup, electroporated at 2200 V, once, 950 µL of 2YT-G was added, and then inhaled into 9 mL of 2YT-G. After recovery at 37° C., 220 rpm, 1 h. 10 µL of sodium ampicillin (Amp) was added and cultured for 1 h. 50 µL of helper phage was added to the bacterial solution and cultured for 2 h. The supernatant was removed by centrifugation, and 10 µL of 2YT-AK was added, suspended, and cultured overnight at 37° C.

B. Coating antigens: antigen was diluted to 2 µg/mL with coating buffer, mixed well, and added into immunotubes, a total of 2.5 mL, and coated at 4° C. overnight.

C. Recombinant phage collection: the overnight culture broth from step A was centrifuged at 6000 g×10 min and the supernatant was filtered through a 0.45 µm filter head. 2 mL of PEG/NaCl was added, mixed well, and placed on ice for diluted anti-M13-Ab-HRP (Sino Biological) was added thereto and allowed to stand for 1 h at 37° C.

D. The 96-well ELISA plate obtained in step C was washed with PBST three times, 100 µL preheated TMB was added, and placed at room temperature for 10 min;

E. The reaction was stopped by adding 50 µL of 1 M H2SO4 and the absorbance was detected at OD450 and the results are shown in Table 1.

TABLE 1

| | | | | | Results of ELISA OD450 detection of phage | | | | | | |
| < > | 1 | 2 | 3 | 4 | 5 | 6 | 7 | 8 | 9 | 10 | 11 | 12 |
|---|---|---|---|---|---|---|---|---|---|---|---|---|
| A | 2.0770 | 2.0530 | 0.3680 | 0.5610 | 2.1900 | 1.9030 | 0.4990 | 1.9170 | 2.0200 | 0.4380 | 2.0340 | 1.9720 |
| B | 0.5290 | 1.9010 | 1.7150 | 1.9060 | 1.7170 | 1.7970 | 1.0610 | 1.7190 | 1.1030 | 0.6380 | 1.9130 | 1.8080 |
| C | 0.1210 | 0.1460 | 1.9680 | 1.9710 | 1.9910 | 1.8860 | 0.2140 | 1.8920 | 0.8290 | 0.5960 | 1.9750 | 1.7840 |
| D | 2.0160 | 2.0810 | 1.9220 | 1.9760 | 0.6060 | 1.9300 | 1.9290 | 2.0310 | 1.9100 | 1.9590 | 0.7920 | 1.8600 |
| E | 1.9490 | 1.9090 | 0.5470 | 1.9890 | 1.9730 | 1.9180 | 0.2890 | 1.9310 | 1.8910 | 1.9690 | 1.0570 | 1.7860 |
| F | 1.9980 | 0.1580 | 1.9850 | 1.9160 | 1.9680 | 1.9680 | 1.8550 | 0.6430 | 1.7690 | 1.6840 | 1.9600 | 1.7760 |
| G | 2.0100 | 1.9800 | 0.4920 | 2.0210 | 2.0070 | 2.0640 | 1.9740 | 1.6270 | 1.9000 | 1.2460 | 1.9270 | 1.8610 |
| H | 2.0320 | 0.6220 | 2.0030 | 2.1240 | 2.0110 | 0.6490 | 1.9920 | 1.9800 | 0.8990 | 0.7020 | 0.9530 | 0.6170 |

30-60 min, centrifuged at 10000 g×20 min, the supernatant was removed, and 5 mL PBS was used to dissolve the phage library.

D. Blocking: the immunotubes, obtained in step B were washed twice with PBS and a blocking solution was added for 1 h at room temperature. In addition, 1 mL of phage library was mixed with an equal volume of blocking solution and blocked at room temperature for 10-15 min.

E. Phage libraries incubation: the immunotubes obtained in step D were washed twice with PBS, added to the blocked phage library, and placed in the incubator at 37° C. for 2-3 h.

F. Elution: the immunotubes obtained in step E were washed eight times with PBST and two times with PBS, and 2.5 mL of eluent (0.2 M glycine, pH 2.5) was added. After standing for 10 min, the eluent was transferred to a 15 mL centrifuge tube and neutralized by adding 500 µL of 1 M Tris-HCl buffer (PH 8.0).

G. Infection: 500 µL of the above eluent was taken, added into 10 ml TG1 bacterial solution, and allowed to stand at 37° C. for 30 min. The bacterial solution Was gradient diluted by 10 times, 100 times, and 1000 times, respectively, 100 uL of the above diluted bacterial solution was taken and plated, and 5 µL of Amp was respectively added to the remaining solution, at 37° C., 220 rpm, 1 h.

H. The next round of Panning: 50 µL helper phage was added to the above bacteria solution at 37° C. for 220 rpm for 2 h. The supernatant was removed by centrifugation at 2500 rpm×5 min and the bacterial suspension mud was blown with 10 ML 2×YT-AK and cultured overnight at 37° C. at 220 rpm. Steps B-G were then repeated for a total of 3 rounds of Panning.

After three rounds of screening, monoclonal antibodies are selected, and the activity of phage is detected by the phage ELISA method, and the specific steps are as follows:

A. CTLA4 protein was coated, diluted to 0.5 µg/mL with coating buffer, mixed well, and added to a 96-well ELISA plate overnight at 4° C.

B. The 96-well ELISA plate obtained in Step A was washed twice with PBST, and 50 µL of L phage supernatant and 50 µL of 1% BSA were added at 37° C. and allowed to stand for 1 h.

C. The 96-well ELISA plate obtained in Step B was washed three times with PBST, and 100 µL of 1:10000

Some positive clones with OD450>2.0 were selected for sequencing. Sequencing results showed that the single domain antibody sequences of all clones were identical, and the single structure antibody was named CA1.

The CA1 sequence contains CDR as shown in SEQ ID NO: 1, SEQ ID NO: 2, and SEQ ID NO: 3.

The full-length single domain amino acid sequence of CA1 is as shown in SEQ ID NO: 4, specifically:

QVQLQESGGGLVQAGGSLRLSCAASGSIFSINHMAWYRQAPGKQRELVAG

VNSRGTTNYVDSVKGRFTISRDNAKNMVYLLMNSLKPEDTAVYYCRALGG

AVAAWGQGTQVTVSS.

Example 2: Humanization of CTLA4 Single Domain Antibody

The specific binding CTLA4 single domain antibody CA1 obtained in Example 1 was humanized according to the following steps:

The framework sequences of IGHV3-23*01 (amino acid sequence as shown in SEQ ID NO: 5) and IGHJ1*01 were chosen as humanized framework sequences. According to the Kabat coding method, the sequence is encoded and the CDR region and FR region are defined. By CDR-grafting, the CDR of CA1 was juxtaposed to the corresponding human-derived FR region sequence, and then the FR region was subjected to reverse mutation of V37Y, W47L, S49A, and K94A to obtain HCA11 (amino acid sequence as shown as SEQ ID NO: 6). Mutations of F27S and T28I were performed on the basis of HCA11 to obtain HCA12 (amino acid sequence as shown in SEQ ID NO: 7). Mutation of A93R was performed on the basis of HCA12 to obtain HCA13 (amino acid sequence as shown in SEQ ID NO: 8). Mutations of G44Q and L45R were performed on the basis of HCA13 to obtain HCA14 (amino acid sequence as shown in SEQ ID NO: 9). In addition, based on HCA13, T77M, and L78V mutations were performed to obtain HCA15 (amino acid sequence as shown in SEQ ID NO: 10).

Example 3: Expression and Preparation of Antibody and Protein

CA1 was expressed as a fusion with FC of IgG4 (where amino acid S at position 228 of IgG4 was mutated to P) and the antibody was named CA1-F4, the amino acid sequence of which is as shown in SEQ ID NO. 11. The DNA fragment of CA1 of the antibody and the DNA fragment of FC of IgG4 were ligated by the PCR method to obtain the full-length CA1-F4 fragment. The CA1-F4 fragment (containing the signal peptide) was cloned into the PCDN A3.1 (Invitrogen) plasmid. CA1-F4 expression plasmid was transiently transfected into the EXP1293 cell line, and the supernatant was purified by Protein A(GE) to obtain a purified antibody.

According to the above-mentioned method, the antibodies were expressed as a fusion of FC of IgG4 (where amino acid S at position 228 of IgG4 was mutated to P), and HCA11, HCA12, HCA13, HCA14, and HCA15 were constructed and prepared, respectively, and named as HCA11-F4 (amino acid sequence as shown in SEQ ID NO: 12), HCA12-F4 (amino acid sequence as shown in SEQ ID NO: 13), HCA13-F4 (amino acid sequence as shown in SEQ ID NO: 14). HCA14-F4 (amino acid sequence as shown in SEQ ID NO: 15) and HCA15-F4 (amino acid sequence as shown in SEQ ID NO: 16). An antibody expressed as a fusion of HCA14 and FC of human IgG1 was constructed, named as HCA14-F1, and its amino acid sequence is as shown in SEQ ID NO: 17.

In addition, an asymmetric FC fusion protein of monovalent HCA14 single domain antibody was constructed and prepared by knobs into holes (KIH) technology, and named as HCA14-KH. The knobs portion of HCA14-KH does not contain the HCA14 single domain and the amino acids of the knobs portion FC are shown in SEQ ID NO. 18. The holes portion of HCA14-KH comprises a single domain of HCA14, the amino acid of which is as shown in SEQ ID NO: 19.

Meanwhile, through conventional molecular manipulation and transient transfection expression in EXP1293 cells, a control antibody with a variable region (heavy chain variable region, the amino acid sequence of which is shown in SEQ ID NO: 20; and a light chain variable region, the amino acid sequence of which is as shown in SEQ ID NO: 21) consistent with Ipilimumab is constructed and prepared, the IgG1 structure of which is named Ipilimumab (IgG1), and the IgG4 structure of which is named Ipilimumab (IgG4).

Example 4: In Vitro Activity Detection of CTLA4 Antibody

1. Binding Activity Assay of Antibody to Human CTLA4 Recombinant Protein

Human CTLA4-His recombinant protein was coated on the ELISA plate overnight at 4° C. After blocking, gradient diluted antibody was added, and reacted at 37° C. for 1 h, after washing twice with PBST, Goat anti-human-IgG-HRP was added, 100 μL per well, reacted at 37° C. for 1 h, and finally, after washing three times with PBST, color development stops after adding TMB, and read at 450 nm with a microplate reader.

As shown in FIG. 1, the protein binding activity showed that different antibodies had different activities with CTLA4 recombinant protein, and the EC50 of CA1-F4 and HCA14-F4 binding to recombinant protein was 6.775 ng/mL and 8.087 ng/ml, respectively, and the EC50 of HCA14-F1 binding to recombinant protein was 0.6364 ng/mL.

2. Binding Activity Assay of Antibody to CTLA4 Expressing Cells

Human CTLA4 expression plasmids were transfected into 293 cells (TaKaRa, lenti-X, 632180) using the PEI transfection method and used every other day. Overexpressing cells were plated in reaction plates, blocked with 1% BSA, and incubated at room temperature for 1 h. Gradient diluted antibody was added, 100 uL/well, incubated at room temperature for 1 h, washed once with PBS, then goat anti-human IgG-HRP (Jackson Immuno) was added, 100 uL/well, reacted at room temperature for 1 h, washed twice with PBS, filially TMB was added to develop color, stop with 1 M sulfuric acid, and read at 450 nm with a microplate reader. Using the same method mentioned above, the binding activity of antibodies to monkey CTLA4 expression cells was detected.

Figure 2:
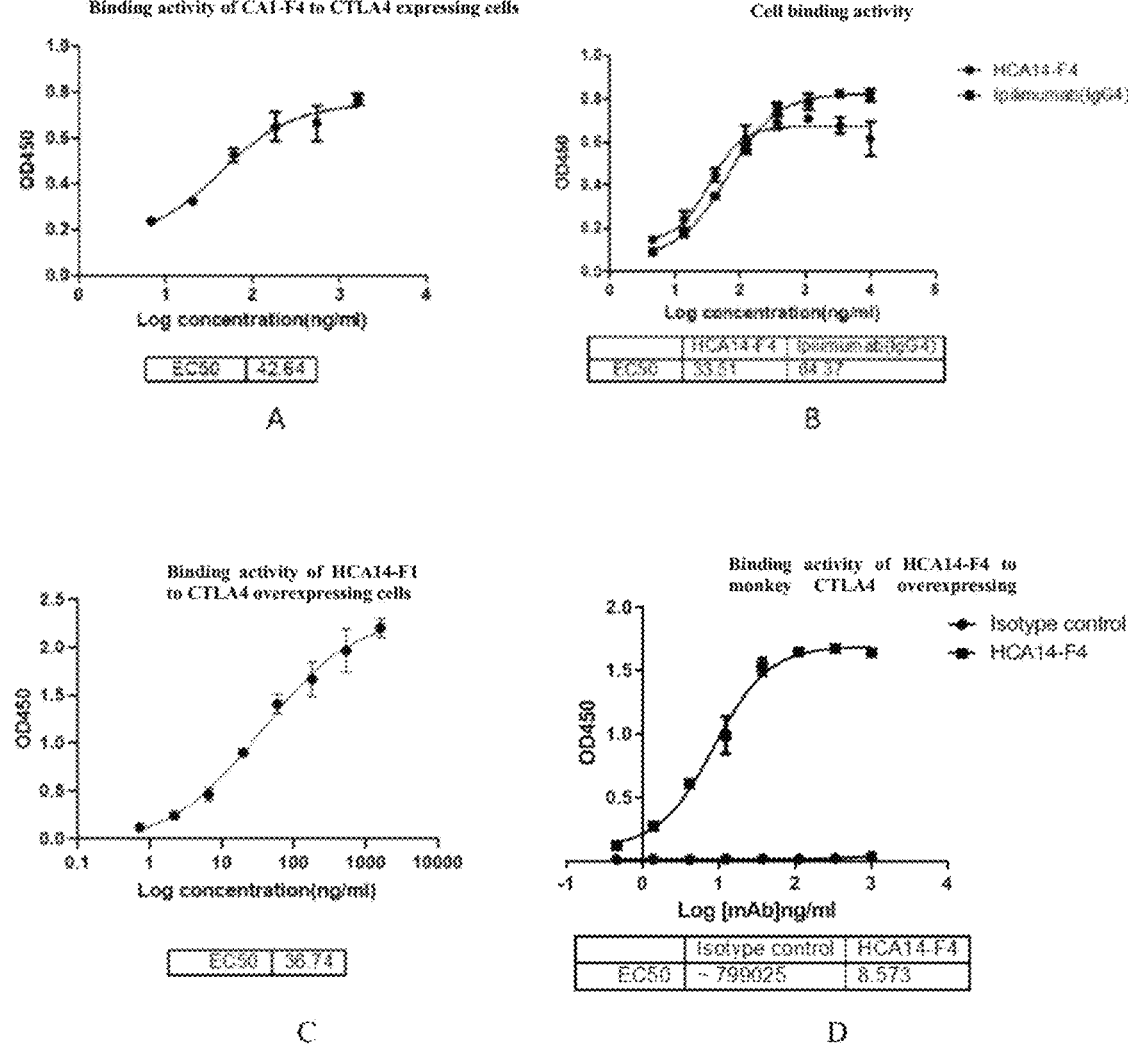
FIG. 2 shows the results of the binding activity of the antibody of Example 4 to cells overexpressing CTLA4; the results showed that the EC50 of CA1-F4 to CTLA4 overexpressing cells was 42.64 ng/mL, the EC50 of HCA14-F4 was 33.51 ng/mL and the EC50 of HCA14-1 was 36.74 ng/mL.

As shown in FIG. 2, cell binding experiments showed that the EC50 for binding, of CA1-F4 and HCA14-F4 to human CTLA4 expressing cells was 42.64 ng/mL and 33.51 ng/mL, respectively, and the cell binding activity of HCA14-F4 was superior to that of the control antibody Ipilimumab (IgG4) (EC50 of 64.37 ng/mL). In addition, the EC50 for cell binding of HCA14-F1 was 36.74 ng/ml. The EC50 for the binding activity of HCA14-F4 to monkey CTLA4 expressing cells was 8.573 ng/ml.

3. Activity Assay of Antibody and Inhibition of CTLA4 Binding With Ligand

Human CTLA4-FC recombinant protein was coated on the ELISA plate overnight at 4° C. and washed twice with PBST. After blocking with 1% BSA and reacted at 37° C. for 1 h and washed twice with PBST. Graded diluted antibodies were added followed by equal volumes of CD86-FC-HIS or CD80-FC-HIS protein, incubated for 1 h, and washed twice with PBST. ANTI-HIS-HRP diluted in 1:10000 was added, incubated at 37° C. for 1 h, and washed with PBST three times. After color development by adding TMB, stop by adding 1 M sulfuric acid, and read at 450 nm by a microplate reader.

Figure 3:
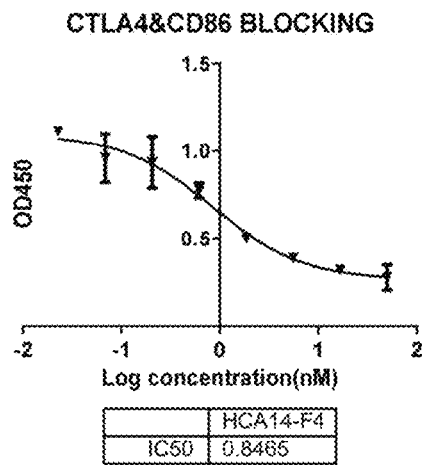
FIG. 3 shows the results of the activity of the antibody of Example 4 to inhibit the binding of CTLA4 to a ligand; the results showed that HCA14-F4 inhibited the binding of CTLA4 to CD86 or CD80 with IC50 values of about 0.84651 nM and 6.17 nM, respectively.
Figure 3:
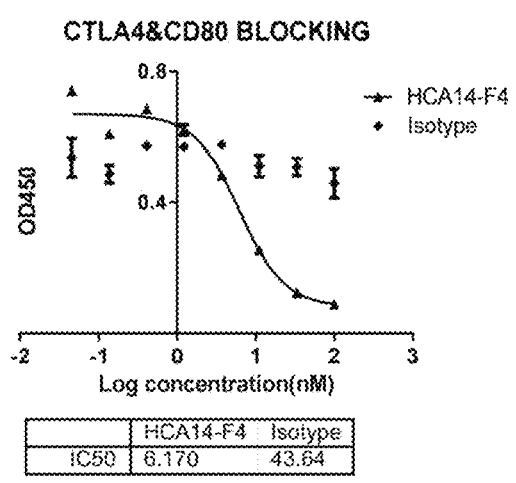

As shown in FIG. 3, binding experiments showed that HCA14-F4 inhibited both CTLA4 binding to CT86 and CTLA4 binding to CD80 with IC50 of 0.8465 nM and 6.17 nM, respectively.

4. Antibodies Affinity Activity Assay

Figure 4:
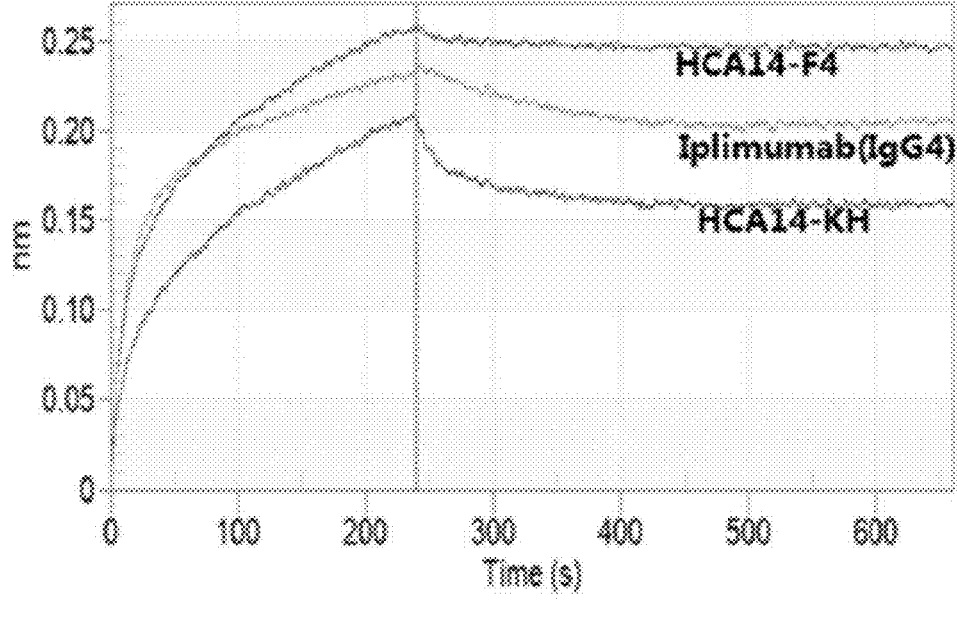
FIG. 4 shows the results, of the affinity detection, of the antibody of Example 4 to CTLA4 recombinant protein. The results showed that the affinity of HCA14-F4 to CTLA4 was better than that of the control antibody.

The affinity constant KD of the antibody to CTLA4 was determined using OCTET. Firstly, the protein A biosensor was used to immobilize the antibody to be detected, and the biosensors containing different antibodies were placed in the CTLA4-HIS diluent with the same concentration (Sino Biological) for binding for 4 min. The biosensor was then placed in the PBS for 400 s. The affinity constant KD of the antibody was analyzed by OCTET analysis software, KD is kd/ka. The results are shown in FIG. 4 and Table 2. The bivalent antibody HCA14-F4 binds faster and dissociates slower than the control antibody Ipilimumab (IgG4). After analysis, the affinity constant KD for the HCA14-F4 curve fit was shown to be less than 1.0E-12M and the affinity was better than ipilimumab (IgG4), with an affinity constant KD of 3.51E-0.9M. In addition, the monovalent antibody HCA14-KB also exhibits fast binding and slow dissociation characteristics.

TABLE 2

| Antibody affinity assay results | | | |
| --- | --- | --- | --- |
| Loading Sample ID | KD (M) | kon(1/Ms) | kdis(1/s) |
| HCA14-F4 | <1.0E-12 | 3.73E+04 | <1.0E-07 |
| HCA14-KH | 1.39E-08 | 3.45E+04 | 4.81E-04 |
| Ipilimumab (IgG4) | 3.51E-09 | 5.98E+04 | 2.10E-04 |

Example 5: Detection of Antibody Functional Activity

1. Mixed Lymphocyte Reaction (MLR) Activity Assay

Figure 5:
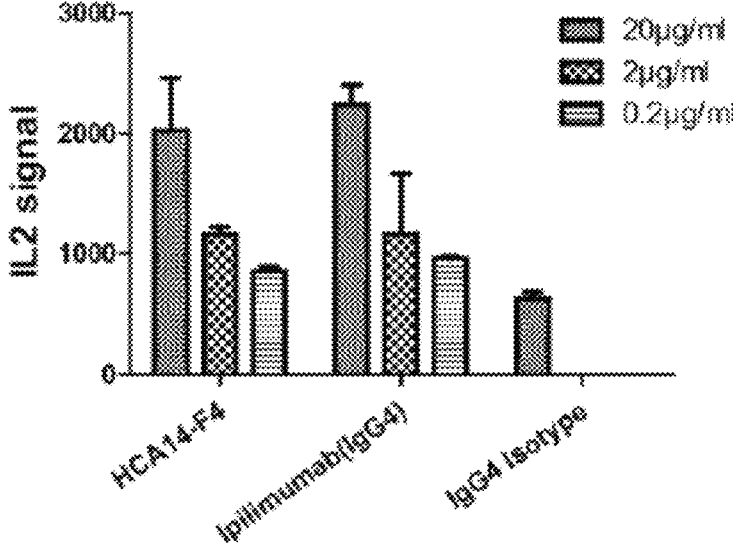
FIG. 5 shows the results of the activity detection of the antibody of Example 5 in the Mixed Lymphocyte Reaction (MLR). The results showed that HCA14-F4 stimulated T cells to secrete IL2.

Stimulation of T lymphocytes by the antibody was detected using the mixed lymphocyte reaction (MLR). Separate the PBMC, first the blood was diluted with PBS buffer solution at 1:1, 3 mL of lymphocyte separation solution was transferred into a centrifuge tube, and 4 mL of diluted blood was added; note that when adding, ensure that the diluted blood is placed on the upper layer of lymphocyte separation solution, and cannot be mixed well. Then, centrifuged at 400 g at RT for 30-40 min. The separated PBMC was finally aspirated and centrifuged at 300 g for 10 min. CD4+ T cells were separated by a CD4+ cell separation kit (BD company) and DC cells were separated by DC cell separation magnetic beads (BD company). Cells were plated at 1×105 CD4+ T cells and 1×104 DC per well in a total volume of 100 μL. Various concentrations of antibody were added and IL-2 concentrations were detected after 5 days of culture using a Human IL-2HTRFkit (Cisbio, cat# 64IL2PEB). The results show (FIG. 5) that HCA14-F4 has an activity to stimulate IL2 secretion comparable to the control antibody.

2. SEB Activity Assay

Figure 6:
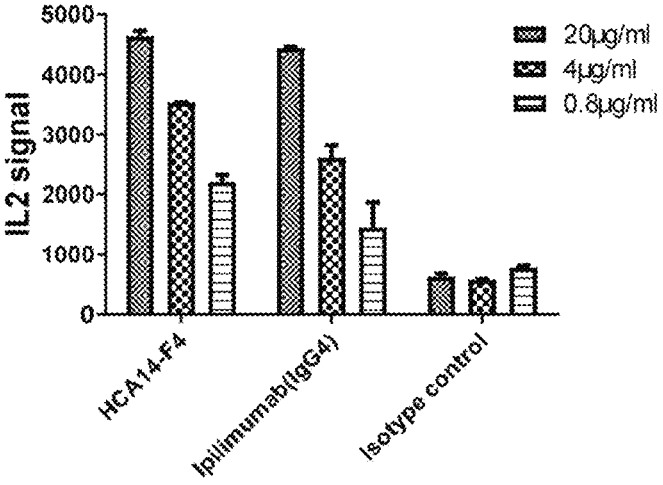
FIG. 6 shows the results of the activity detection of the antibody of Example 5 in the SEB assay. The results showed that HCA14 stimulated PBMC cells to secrete IL2, which was better than the control antibody.

Antibody activity was detected by the staphylococcal enterotoxin B (SEB) stimulation method. First, human PBMC was isolated, PBMC was mixed with Staphylococcal enterotoxin B (SEB), various, concentrations of antibodies to be detected or control antibodies were added, and after 3-5 days of culture, IL-2 was detected using the Human IL-2HTRF kit (Cisbio, cat# 64IL2PEB). The results showed (FIG. 6) that HCA14 stimulated IL2 secretion with activity superior to the control antibody Ipilimumab. The negative control had no stimulatory activity.

Figure 7:
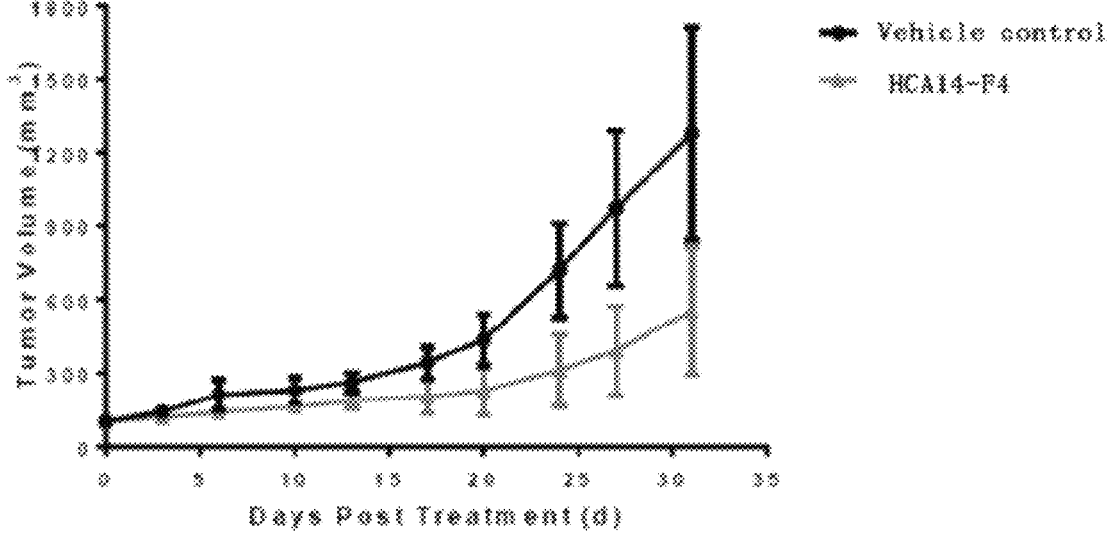
FIG. 7 shows the in vivo tumor inhibitory activity of the antibody of Example 6 in the hPD1/hCTLA4 transgenic C57BL/6J mouse model. The results showed that HCA14-F4 significantly inhibited the growth of MC38 xenografts.

Example 6: In Vivo Tumor Models Treated with CTLA4 Antibody hPD1/hCTLA4transgenic C57BL/6J mice were used as a mouse model to examine the in vivo effect of CTLA4 antibody on tumor growth. MC38 cells in the logarithmic growth phase were collected, and the culture medium was removed and washed twice with PBS and inoculated into mice at an inoculum size of 5×105/100 μL/mouse (without matrigel). After the mean tumor volume reached about 100 mm3, the mice with tumor volume reaching the grouping criteria were randomly divided into 2 groups, namely Vehicle control and the drug to be detected (HCA14-F4 in PBS), and then began to administer the drug. The administration cycle was Q3D×8. The way of administration is IP, and the dosage is 1.2 mg/kg. Mice body weight and tumor volume were measured on the day of administration, once every 3 days for 8 doses. When tumors reached the tumor endpoint (1500 mm3) or showed more than 15% weight loss, the experiment was terminated and all mice were euthanized. The results showed (FIG. 7) that HCA14-F4 significantly inhibited MC38 xenograft tumor growth in a transgenic mouse tumor model, showing significant tumor inhibitory activity.

While the invention has been described in connection with what is presently considered to be the most practical and preferred embodiments, it is to be understood that the invention is not limited to the disclosed embodiments, but, on the contrary, is intended to cover various modifications and equivalent arrangements included within the spirit and scope of the appended claims.

The antibodies of the present invention can be made using genetic engineering techniques, as the DNA sequences encoding the humanized antibodies of the present invention can be obtained by conventional means well known to those: skilled in the art, e.g. according to the amino acid sequences disclosed herein or by amplification using the PCR method, and thus recombinant DNA methods can also be used, and the sequences can be ligated into suitable expression vectors by a variety of methods well known in the art.

Once the antibody molecules of the invention are prepared, they can be purified by any method known in the art for purifying immunoglobulin molecules, e.g. by chromatography (e.g. ion exchange chromatography, affinity chromatography, particularly by protein A affinity chromatography and other column chromatography), centrifugation, use of solubility differences, or by any other standard technique for purifying proteins. In many embodiments, the antibody is secreted from the cells into the culture medium and the antibody is purified by harvesting the culture medium.

By at least 90% overall sequence identity in the context of the present invention is meant that the sequence identity is 91%, 92%, 93% 94%, 95%, 96%, 97% 98%, 99% or 100%, and in the context of the present invention the single domain antibody amino acid sequence SEQ ID NO: 4 or SEQ ID NO: 9 has at least 90% overall sequence identity, and it is meant that the sum of the amino acid sequences of the antibody heavy chain variable region or VHH single domain antibody variable region has at least 90% overall sequence identity to the sum of the sequences of the amino acid sequences SEQ ID NO: 4 or SEQ ID NO: 9.

The CTLA4 single domain antibody of the present invention, as well as the CTLA4 single domain antibody, can also be used for scientific research related to CTLA4, such as scientific research in various fields such as developmental biology, cell biology, metabolism, structural biology, functional genomics, or medical and pharmaceutical applications such as tumors, autoimmune diseases, etc.

The CTLA4 antibodies of the present invention may be single-chain antibodies, double-chain antibodies, chimeric antibodies, humanized antibodies, as well as derivatives, functional equivalents, and homologs of the foregoing, including antibody fragments and any polypeptide comprising an antigen binding domain.

The pharmaceutical compositions of the present invention further comprise a pharmaceutically acceptable carrier and/or diluent.

The invention can also be a reagent or chip comprising the aforementioned CTLA4 antibody.

The present invention also discloses methods of using the CTLA4 single domain antibody for binding to an antigenic site of a target cell and stimulating the activity of PBMC and T cells, anti-tumor activity, and the use of the antibody in the treatment of related diseases or related diagnostics and detections using kits containing the antibody.

In the present invention, unless otherwise indicated, scientific and technical terms used herein have the meanings commonly understood by those skilled in the art. Refer to standard manuals such as Sambrook et al. Molecular Cloning: A Laboratory Manual (2nd ed.), vol. 1-3, Cold Spring Harbor Laboratory Press (1989); Lewin, GenesIV, Oxford University Press, New York, (1990); Roitt et al. Immunology (2nd ed.), GowerMedical Publishing, London, New York (1989). Also, as used herein, protein and nucleic acid chemistry, molecular biology, cell and tissue culture, microbiology, immunology, and laboratory procedures are terms and procedures widely used in the pertinent art. Meanwhile, definitions and explanations of related terms are provided below for a better understanding of the present invention.

Antibody

The term "antibody" refers broadly to any immunoglobulin molecule or antigen-binding portion thereof, and unless otherwise specified, the terms "antibody" or "immunoglobulin", which may be used interchangeably herein, whether referring to a heavy chain antibody or a conventional 4-chain antibody, are used as a general term to include full-length antibodies, individual chains thereof, and all portions, domains or fragments thereof (including but not limited to antigen-binding domains or fragments, such as VHH domains or VH/VL domains, respectively).

Variable Region

The term "variable region" as used herein refers to an antibody variable region consisting essentially of four framework regions referred to in the art and hereinafter as framework region 1 or FR1, framework region 2 or FR2, framework region 3 or FR3, and framework region 4 or FR4, respectively, wherein the framework regions are separated by three complementarity-determining regions or CDR referred to in the art and hereinafter as complementarity-determining region 1 or CDR1, complementarily-determining region 2 or CDR2, and complementarity-determining region 3 or CDR3. Thus, a stretch or sequence of an antibody variable region can be represented as follows: FR1-CDR1-FR2-CDR2-FR3-CDR3-FR4. The antibody variable region confers antigen specificity to the antibody by virtue of having an antigen-binding site. The framework region adopts a beta-sheet conformation, and the CDR may form a loop linking the beta-sheet structure. The CDR in each chain are held in their three-dimensional structure by the framework regions and together with the CDR of the other chain form an antigen-binding site.

Domain

As used, herein, the term "domain" (of as polypeptide or protein) refers to a folded protein structure that is capable of maintaining its tertiary structure independent of the rest of the protein. Generally, a domain is responsible for a single functional property of a protein, and in many cases can be added, removed, or transferred to other proteins without loss of the function of the rest of the protein and/or the domain.

Single Domain Antibody

As used herein, the term "single domain antibody" refers to an immunoglobulin variable region capable of specifically binding an epitope without pairing it with other immunoglobulin variable regions.

VHH

"VHH", also known as heavy chain structural antibodies, VHH domains, VH antibody fragments, and VHH antibodies, are variable domains of antigen-binding immunoglobulins called "heavy chain antibodies" (i.e. "antibodies lacking the light chain") (Hamers-Casterman C, Atarhouch T, Muyldemans S, Robinson G, Hankrs C, Songa E B, Bendahman N, Hamer R.:Naturally occurring antibodies devoid of light chains; Nature363, 446-448(1993)). The term "VHH" is used to distinguish the variable region from the heavy chain variable region present in conventional 4-chain antibodies and the light chain variable region present in conventional 4-chain antibodies. The VHH domain specifically binds to an epitope without the need for other antigen-binding domains (unlike the VH or VL domains in conventional chain antibodies, in which ease the following epitope is recognized by the VH domain together with the VL domain). The VHH domain is a small, stable, and efficient antigen recognition unit formed by a single immunoglobulin domain.

In the context of the present invention, the terms "heavy chain single domain antibody", "VHH domain", "VHH", "VHH antibody", and "VHH antibody fragment" are used interchangeably.

The amino acid residues used for the VHH domain of Camelidae are numbered according to the general numbering of VH domains given by Kabat et al, (Sequence of proteins of immunological interest, Us Public Health Services, NIH Bethesda, MD, publication No. 91). According to this numbering, FR1 comprises amino acid residues at positions 1-30, CDR1 comprises amino acid residues at positions 31-35, FR2 comprises amino acids at positions 36-49, CDR2 comprises amino acid residues at positions 50-65, FR3 comprises amino acid residues, at positions 66-94, CDR3 comprises amino acid residues at positions 95-102, and FR4 comprises amino acid residues at positions 103-113.

It should be noted, however, that as is well known in the art for VH domains and VHH domains, the total number of amino acid residues in each CDR may differ and may not correspond to the total number of amino acid residues indicated by the Kabat numbering (i.e. one or more positions according to the Kabat numbering may not be occupied in the actual sequence, or the actual sequence may contain more amino acid residues than allowed by the Kabat numbering). This means that in general, the numbering according to Kabat may or may not correspond to the actual numbering of the amino acid residues in the actual sequence.

Alternatives to numbering the amino acid residues of the VH domain are known in the art and can be similarly applied to the VHH domain. However, unless otherwise indicated in the specification, claims, and drawings, the numbering according to Kabat and as applicable to VHH domains as described above will be followed.

The total number of amino acid residues in the VHH domain will typically range from 110 to 120, often between 112 and 115. It should be noted, however, that smaller and longer sequences may also be suitable for the purposes described herein.

Other structural and functional properties of VHH domains and polypeptides containing them can be summarized as follows: the VHH domain, which has been naturally "designed" to functionally bind to an antigen in the absence of and without interaction with the light chain variable domain, can be used as a single and relatively small functional antigen-binding building block, domain or polypeptide. This distinguishes the VHH domain from the VH and VL domains of conventional 4-chain antibodies, which themselves are generally not suitable for practical use as a single antigen binding protein or immunoglobulin single variable domain, but need to be combined in some form or another to provide a functional antigen binding unit (e.g. in the form of a conventional antibody fragment such as a Fab fragment; or in the form of anscFv consisting of a VH domain covalently linked to a VL domain). A VHH domain requires only a single domain to bind an antigen with high affinity and high selectivity, thus requiring neither the presence of two separate domains nor ensuring that the two domains are present in the proper spatial conformation and configuration (e.g.seFv typically requires the use of a specially designed linker).

The VHH domain can be humanized by CDR grafting, i.e. grafting the CDR sequence of the VHH domain onto the FR framework sequence of the VH domain of a human conventional 4-chain antibody. The humanized VHH domain may contain one or more fully human framework sequences, and in a particular embodiment may contain the human framework sequences of IGHV3. Other modifications may also be made within the human framework sequence.

Knobs Into Holes

The term "Knobs into holes", as used herein, refers to the use of genetic engineering techniques to mutate one of the heavy chain CH3 of an antibody by a knob and another heavy chain CH3 by a hole to facilitate the biting of the two heavy chains to form a heterodimer.

Sequence

As used herein, the term "sequence" is generally understood to include both the relevant amino acid sequence and the nucleic acid or nucleotide sequence encoding the sequence, unless the context requires a more limited explanation.

Specificity

In general, the term "specificity" refers to the number of different types of antigens or epitopes to which a particular antigen-binding molecule or antigen-binding protein (e.g. an immunoglobulin single variable domain of the present invention) can bind. Specificity can be determined based on the affinity and/or avidity of the antigen-binding protein. The affinity, expressed as the dissociation equilibrium constant (KD) of the antigen from the antigen binding protein, is a measure of the binding strength between the epitope and the antigen binding site on the antigen binding protein: the smaller the KD value, the stronger the binding strength between the epitope and the antigen binding protein (alternatively, the affinity can also be expressed as an association constant (KA), which is 1/KD). As will be appreciated by those skilled in the art, affinity assay can be performed in a known manner depending on the particular antigen of interest. Affinity is a measure of the strength of binding between an antigen-binding protein (e.g. an immunoglobulin, an antibody, a single domain antibody, or a polypeptide comprising the same) and an antigen of interest. Affinity is related to both: the affinity between antigen binding sites on its antigen binding protein, and the number of relevant binding sites present on the antigen binding protein.

Epitope

The term "epitope" refers to a protein determinant capable of specifically binding to an antibody. Epitopes generally consist of chemically active surface groups of molecules such as amino acids or sugar side chains and epitopes generally have specific three-dimensional structural features, as well as specific charge characteristics. Conformational and non-conformational epitopes differ in that binding to the former is lost in the presence of denaturing solvents, but binding to the latter is not lost.

The term "epitope" refers to an antigenic moiety capable of specifically binding an antibody or a T cell receptor or otherwise interacting with a molecule. An "epitope" is also referred to in the art as an "antigenic determinant". Epitopes generally consist of a chemically active surface collection of molecules such as amino acids or carbohydrates or sugar side chains. Epitopes may be "linear" or "non-linear/conformational". Once the desired epitope is determined (e.g. by epitope mapping), antibodies to the epitope can be generated. The generation and characterization of antibodies can also provide information about the desired epitope. Based on this information, antibodies that bind to the same epitope can then be screened, e.g. by cross-competition studies, to find antibodies that compete for binding to each other, i.e. antibodies that compete for binding to an antigen.

Pharmaceutical Compositions

The invention provides pharmaceutical compositions comprising one or a combination of the CTLA4 antibodies of the invention formulated together with a pharmaceutically acceptable carrier. Such compositions may comprise one or a combination of (e.g. two or more different) CTLA4 antibodies of the invention. For example, a pharmaceutical composition of the invention may comprise a combination of antibody molecules that bind to different epitopes on a target antigen.

The pharmaceutical compositions of the present invention may also be administered in combination therapy, i.e. in combination with other agents. For example, combination therapy can include a CTLA4 antibody of the invention in combination with at least one other anti-tumor drug. For example, the CTLA4 antibodies of the invention can be used in combination with antibodies that target other tumor-specific antigens. Such antibodies that target other tumor-specific antigens include but are not limited to, anti-CLAU-DIN18.2 antibodies, anti-EGFR antibodies, anti-VEGF antibodies, anti-HER2 antibodies, or anti-C-MET antibodies. Preferably, the antibody is a monoclonal antibody. The CTLA4 antibodies of the present invention can also be used in combination with other tumor immunotherapy approaches, or tumor-targeting small molecule drugs. Such other tumor immunotherapy approaches include but are not limited to, therapeutic antibodies directed against tumor immunomodulatory molecules, such as LAG3, PDL1/PD1, CD137, etc., or CAR-T therapeutic approaches, etc.

The pharmaceutical compositions of the present invention may also be used in combination with, or before or after, other tumor treatment modalities, such as radiotherapy, chemotherapy, surgery, etc.

Disease Prevention and Treatment

In another aspect, the invention provides the use and methods of the CTLA4 antibodies and pharmaceutical compositions of the invention for preventing and/or treating diseases associated with CTLA4. CTLA4-associated diseases that can be prevented and/or treated with the CTLA4 antibodies of the invention are set forth below.

Cancer

Blocking of CTLA4 by the CTLA4 antibodies of the invention can enhance the immune response to tumor cells in a patient. The CTLA4 antibodies of the present invention can be used alone to inhibit the growth of cancerous tumors. Alternatively, as described below, the CTLA4 antibodies of the invention can be used in combination with other anti-tumor therapies, e.g. with other immunogenic agents, standard cancer therapies, or other antibody molecules.

Preferred cancers that can be prevented and/or treated using the CTLA4 antibodies of the present invention include cancers that generally respond to immunotherapy. Non-limiting examples of preferred cancers that can be treated include rectal cancer, melanoma (e.g. metastatic malignant melanoma), lung cancer, ovarian, colon cancer, renal cancer, bladder cancer, breast cancer, liver cancer, lymphoma, gastric cancer, nasopharyngeal cancer, laryngeal cancer, hematologic malignancies, head and neck cancer, glioma, cervical cancer, uterine body tumor, and osteosarcoma. Examples of other cancers that may be treated by the methods of the invention include uterine cancer, anal region cancer, bone cancer, pancreatic cancer, skin cancer, prostate cancer, malignant melanoma of the skin or eye, testicular cancer, fallopian tube cancer, endometrial cancer, vaginal cancer, non-Hodgkin's lymphoma, esophageal cancer, vulval cancer, Hodgkin's disease, adrenal cancer, soft tissue sarcoma, urethral cancer, penile cancer, endocrine system cancer, thyroid cancer, parathyroid cancer, chronic or acute leukemia (including acute cell-like leukemia, chronic myeloid leukemia, acute lymphoblastic leukemia, chronic lymphocytic leukemia), lymphocytic lymphoma, bladder cancer, renal or ureteral cancer, renal cancer, central nervous system (CNS) tumor, primary CNS lymphoma, spinal tumor, brain stem glioma, pituitary adenoma, Kaposi's sarcoma, epidermoid carcinoma, squamous cell carcinoma, T-cell lymphoma, and combinations of the cancers.

The CTLA4 antibodies of the present invention can also be used in combination with immunogenic agents such as cancer cells, purified tumor antigens (including recombinant proteins, peptides, and carbohydrate molecules, cells transfected with genes encoding immunostimulatory cytokines), including but not limited to peptides of melanoma antigens such as Trp-2, the peptide of gp100, MAGE antigens, MART1 and/or tyrosinase, or tumor cells transfected to express the cytokine GM-CSF, etc.

The CTLA4 antibodies of the present invention can also be used in combination with tumor antigens, tumor vaccines, recombinantly produced tumor-specific proteins, and/or peptides to generate an immune response against these proteins. These proteins are normally seen as self-antigens by the immune system and are therefore tolerant to them. A tumor antigen can also be a new antigen expressed by a cancer cell, such as a protein sequence altered by somatic mutation or a fusion protein resulting in two unrelated sequences (e.g. Bcrabl in the Philadelphia chromosome). Other tumor vaccines may include proteins from viruses associated with human cancer, such as human papillomavirus (HPV), hepatitis virus (HBV and HCV), and Kaposi's herpes sarcoma virus (KHSV). The CTLA4 antibody can also be used in combination with purified heat shock protein (HSP) isolated from the tumor tissue itself. These heat shock proteins, which contain fragments of proteins derived from tumor cells, are very effective in delivering to antigen-presenting cells to elicit tumor immunity.

The CTLA4 antibodies of the present invention can also be combined with CAR-T cell therapy to activate a stronger anti-tumor response. CART, known collectively as chimeric antigen receptor T-cell immunotherapy, is an effective cellular therapy method for malignancies.

The CTLA4 antibodies of the invention can also be combined with standard cancer therapies. The CTLA4 antibodies of the present invention can be effectively combined with chemotherapeutic regimens. The scientific rationale for the combination of the CTLA4 antibody of the present invention and chemotherapy is cell death, which is the result of the cytotoxic effects of most chemotherapeutic compounds and should result in elevated tumor antigen levels in the antigen presentation pathway. Angiogenesis inhibitors can also be combined with the CTLA4 antibodies of the invention, and inhibition of angiogenesis results in the death of tumor cells, which can provide tumor antigens to the host's antigen-presenting pathway.

The CTLA4 antibodies of the invention may also be combined with other forms of immunotherapy such as cytokine therapy (e.g. interferon, IL-2, IL-12, GM-CSF, G-CSF) or bispecific antibody therapy to enhance the presentation of tumor antigens.

The CTLA4 antibodies of the invention may also be used in combination with antibodies that target other tumor-specific antigens. Such antibodies that target other tumor-specific antigens include but are not limited to, anti-PDL1 antibodies, anti-EGFR antibodies, anti-CLAUDIN18.2 antibodies, anti-HER2 antibodies, anti-VEGF antibodies, or anti-C-MET antibodies. Preferably, the antibody is a monoclonal antibody.

Infectious Disease

Other methods of the invention are used to treat patients exposed to a particular toxin or pathogen. Accordingly, another aspect of the present invention provides a method of preventing and/or treating an infectious disease in a subject, comprising administering the subject the CTLA4 antibody of the present invention, such that the infectious disease in the subject is prevented and/or treated.

Similar to the use of tumors described above, the CTLA4 antibody may be used alone or as an adjuvant in combination with a vaccine to stimulate an immune response to pathogens, toxins, and self-antigens. Examples of pathogens for which this method of treatment may be particularly useful include pathogens that are not currently effective vaccines, or pathogens that are not fully effective with conventional vaccines. These include but are not limited to, COVID-19, hepatitis viruses (A, B, C), HIV, influenza viruses, herpes viruses, giardia, malaria, *Staphylococcus aureus, Pseudomonas aeruginosa*, and leishmania. The CTLA4 antibody is particularly useful against established infections by pathogens such as HIV, which present altered antigens during the infection. When anti-human CTLA4 antibodies are administered, these new epitopes are recognized as foreign, thereby eliciting a strong T-cell response that is not affected by the negative signal of CTLA4.

Some examples of pathogenic viruses that cause infectious diseases that can be treated using the methods of the present invention include COVID-19, adenovirus, influenza virus, arbovirus, echovirus, rhinovirus, coxsackievirus, coronavirus, hepatitis (A, B, C), herpes virus, respiratory syncytial virus, mumps virus, rotavirus, papillomavirus, measles virus, rubella virus, parvovirus, poliovirus, rabies virus, vaccinia virus, HTLV virus, dengue virus, JC virus, molluscum virus, and arbovirus encephalitis virus.

Some examples of pathogenic bacteria that cause infectious diseases that can be treated using the methods of the present invention include staphylococcus, chlamydia, proteus, ralstonia, rickettsia, mycobacterium, streptococcus, pneumococcus, meningococcus and gonococcus, klebsiella, tetanus bacillus, botulinum, pseudomonas, legionella, corynebacteria diphtheriae, salmonella, bacillus, cholera bacteria, bacillus anthracis, *Yersinia pestis*, leptospira, and Lyme disease bacteria.

Some examples of pathogenic parasites that cause infectious diseases that can be treated using the methods of the present invention include balantidium coil, entamoeba histolytica, *Plasmodium vivax*, nigeriafrugiperda, acanthamoeba spp., trypanosomacruzi, *Leishmania donovani, Toxoplasma gondii, Cryptosporidium* spp., *Pneumocystis carinii*, babesia, trypanosoma brucci, *Giardia lamblia*, and nippostrongylusbrasiliensis.

Some examples of pathogenic fungi that cause infectious diseases that can be treated using the methods of the present invention include candida (*Candida albicans, Candida krusei, Candida glabrata, Candida tropicalis*, etc.), blastomyces dermatitidis, mucor (mucor, absidia, rhizopus), *Cryptococcus neoformans*, paracoccidioidesbrasiliensis, aspergillus (*Aspergillus fumigatus, Aspergillus niger*, etc.), sporothrixschenckii, *Histoplasma capsulatum*, and coccidioidesimmitis.

What is claimed is:

1. An antibody that specifically binds to human CTLA4, comprising three complementarity-determining regions; the three complementarity-determining regions are respectively: CDR1 with the amino acid sequence as shown in SEQ ID NO: 1, CDR2 with the amino acid sequence as shown in SEQ ID NO: 2, and CDR3 with the amino acid sequence as shown in SEQ ID NO: 3.

2. The antibody of claim 1, wherein the antibody is a single domain antibody.

3. The antibody of claim 2, wherein the antibody is a heavy chain single domain antibody.

4. The antibody of claim 2, wherein the single domain antibody comprises any one of the following amino acid sequences: SEQ ID NO: 4, SEQ ID NO: 8, SEQ ID NO: 9, or SEQ ID NO: 10.

5. The antibody of claim 4, wherein the amino acid sequence of the single domain antibody has at least 90% overall sequence identity to amino acid sequence SEQ ID NO: 4 or SEQ ID NO: 9.

6. The antibody of claim 1, further comprising an immunoglobulin FC region.

7. The antibody of claim 6, wherein the immunoglobulin FC region is a human immunoglobulin FC region.

8. The antibody of claim 7, wherein the human immunoglobulin FC region is the FC region of human IgG1 or IgG4.

9. The antibody of claim 7, comprising any one of the following amino acid sequences: SEQ ID NO: 11, SEQ ID NO: 14, SEQ ID NO: 15, SEQ ID NO: 16, SEQ ID NO: 17.

10. A pharmaceutical composition, comprising the antibody that specifically binds to human CTLA4 of claim 1, for the treatment or alleviation of cancer and/or infectious diseases.

11. Use of the antibody that specifically binds to human CTLA4 of claim 1 in the manufacture of a medicament.

12. A kit, comprising the antibody that specifically binds to human CTLA4 of claim 1, for the diagnosis of a CTLA4-related disease; the CTLA4-associated disease is a tumor and/or infectious disease associated with high expression of CTLA4.

* * * * *